US005555284A

United States Patent [19]
Kishigami

[11] Patent Number: 5,555,284
[45] Date of Patent: Sep. 10, 1996

[54] ROENTGENOGRAPHY OF VERTEBRAL COLUMN AND THE DEVICES USED THEREFOR

[76] Inventor: Yoshihiro Kishigami, 1-6-1, Maruyama Dr., Abeno-ku, Osaka, Japan

[21] Appl. No.: 357,584

[22] Filed: Dec. 16, 1994

[51] Int. Cl.$^6$ ................................................ G03B 12/02
[52] U.S. Cl. .......................... 378/177; 378/182; 378/209
[58] Field of Search ................................. 378/177, 167, 378/182, 188, 208, 209

[56] References Cited

U.S. PATENT DOCUMENTS

| | | | |
|---|---|---|---|
| 1,768,769 | 7/1930 | Kelley | 378/209 X |
| 2,656,469 | 10/1953 | Laur | 378/208 X |
| 4,156,145 | 5/1979 | Weatherholt | 378/177 |
| 4,665,574 | 5/1987 | Filips et al. | 378/177 X |
| 4,669,106 | 5/1987 | Ammerman | 378/208 |
| 5,365,565 | 11/1994 | Barbaric | 378/177 X |

OTHER PUBLICATIONS

Lloyd, Ray D. et al., "Design and Calibration of a Total-Body Counting System for Measuring Radioactivity in Beagles", International Journal of Applied Radiation and Isotopes, Feb. 1976, vol. 27, pp. 103–111.

Primary Examiner—David P. Porta

[57] ABSTRACT

A roentgenography and a device used therefor by which shapes of the vertebral columns of vertebrate animal including Homo sapiens can be clearly photographed when once photographed for the sake of positively diagnosing an affected part of disc hernia and the like. The roentgenography is carried out by laying a patient vertebrate animal on a concavely curved X-ray film the radius of curvature of which is equal to a distance between the X-ray film and an X-ray tube positioned over the same to curve the vertebral column of the patient into a circularly arced shape, and irradiating perpendicularly X-ray from the center of this circular arc upon the vertebral column. The device used for executing the above roentgenography is either a curved photographic stand provided with a top which is concavely formed in such that the radius of curvature of the concave shape is equal to a difference between the top and an X-ray tube positioned over the same or a concavely curved cassette which is concavely formed in such that the radius of curvature of the concave shape is equal to a difference between the cassette and an X-ray tube positioned over the same.

2 Claims, 7 Drawing Sheets

ROENTGENOGRAPHY OF VERTEBRAL COLUMN AND THE DEVICES USED THEREFOR

BACKGROUND OF THE INVENTION

1. Field of the Invention

This invention relates to a roentgenography of flexible skeletons, especially vertebral columns (backbones) of vertebrate animal including Homo sapiens and the devices used therefor, and more particularly to a roentgenography and the devices used therefor by which the shape of a vertebral column can be clearly photographed in such that X-ray patterns of the adjacent vertebrae are not overlapped one another by utilizing such a characteristic of a vertebral column composed of cervical vertebrae, thoracic spines, lumbar vertebrae and the like that the column may be artificially curved.

2. Description of the Related Art

Figure 10:
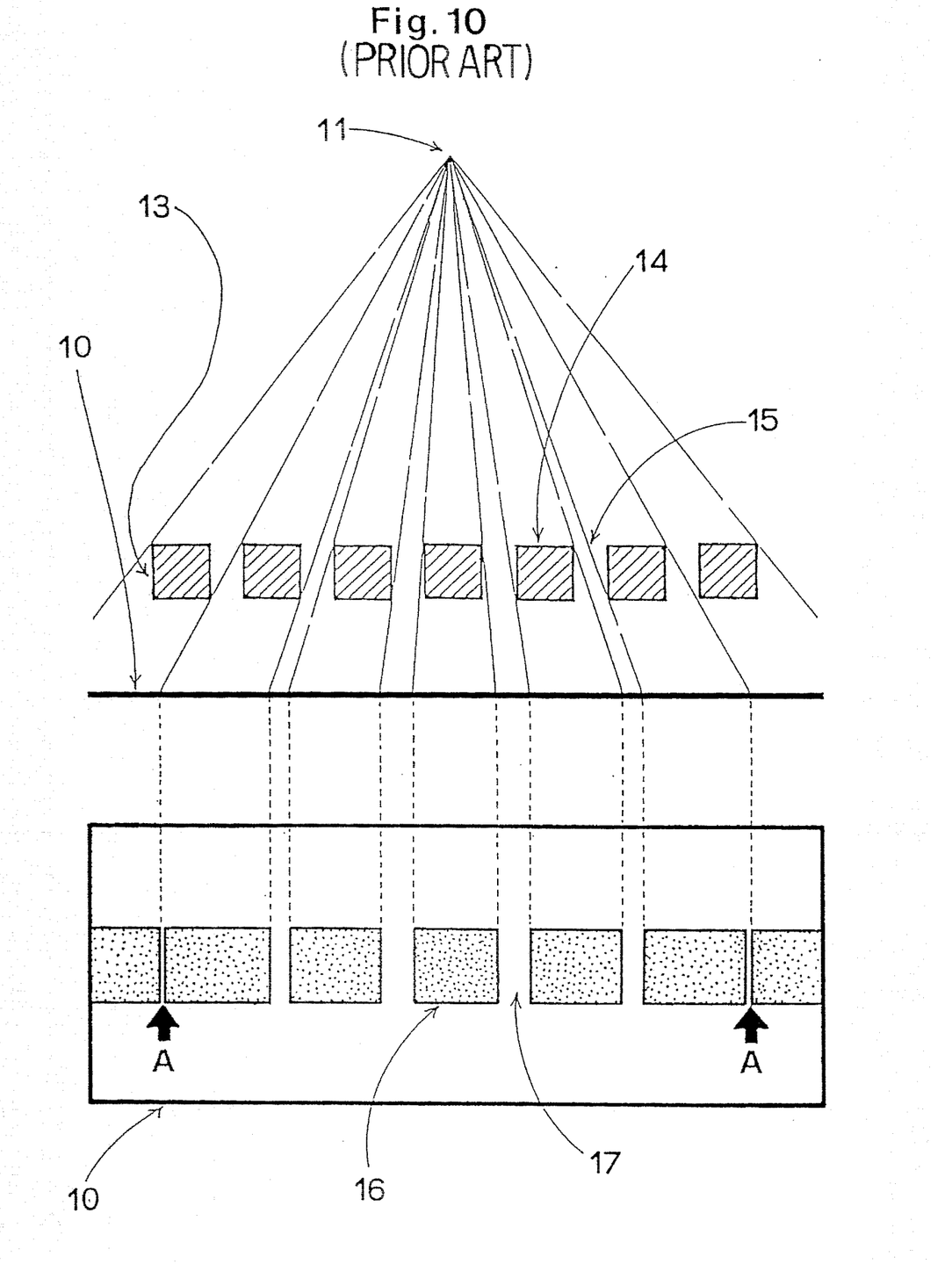
FIG. 10 is a schematic view for explaining a disadvantage involved in a prior art roentgenography.

In even the latest technology in which bones are photographed by the use of X-ray to precisely determine forms of the bones from the images thereof which have been taken on films, X-ray films are applied while maintaining the same in a planar state which remains unchanged. In this manner, however, there arises an extremely inconvenient problem, when a vertebral column composed of a number of continuous vertebrae is photographed by the use of a conventional flat photographic stand. More specifically, as schematically shown in FIG. 10, both of a vertebra shadow 16 and an intervertebral space shadow 17 are clearly photographed in the central portion of an X-ray film 10, while vertebra shadows 16 positioned near to the opposite end portions of the X-ray film comes to extend lengthily so that the resulting intervertebral space shadows 17 become obscure as indicated by arrows A. In this connection, for the sake of simple explanation, vertebrae 14 are illustrated by simple cubes, besides it is illustrated in such that a length of an intervertebral space 15 is extremely broaden and a distance between an X-ray film 10 and an X-ray tube 11 is far shorter than that in reality in FIG. 10. While the illustration has been made exaggeratedly in FIG. 10, in short, the vertebrae positioned immediately below the X-ray tube 11 are clearly photographed because the pattern of such a vertebra is not covered by shadows of both the adjacent vertebrae. On the contrary, X-ray comes to be irradiated more obliquely with increase in a distance from the X-ray tube 11, so that vertebral shadows 16 positioned near to the opposite ends of the X-ray film 10 extend lengthily. As a result, the adjacent vertebra shadows positioned near to the opposite ends of the film are overlapped one another as described above, so that the intervertebral space shadows 17 positioned near to the opposite ends of the film become obscure.

Because of the above described disadvantage involved in the conventional flat photographic stand, an affected part of disc hernia could not be heretofore ascertained by a shot of photographing in case of, for example, making a diagnosis of such disc hernia. Although an approximate position of the affected part can be decided by a prior neurological examination therefor, in order to make a more positive diagnosis it is required that roentgenograms are taken several times while shifting from an expected position little by little to obtain slightly different patterns on several films, and the resulting patterns on the several films are checked to collectively judge the affected part. As a result, roentgenographic engineers who take roentgenograms and physicians or veterinary surgeons who read such roentgenograms require extra labor, and further extra expenses for films and the development therefor are required, besides it results in three to four times higher X-irradiation upon patients.

Figure 11:
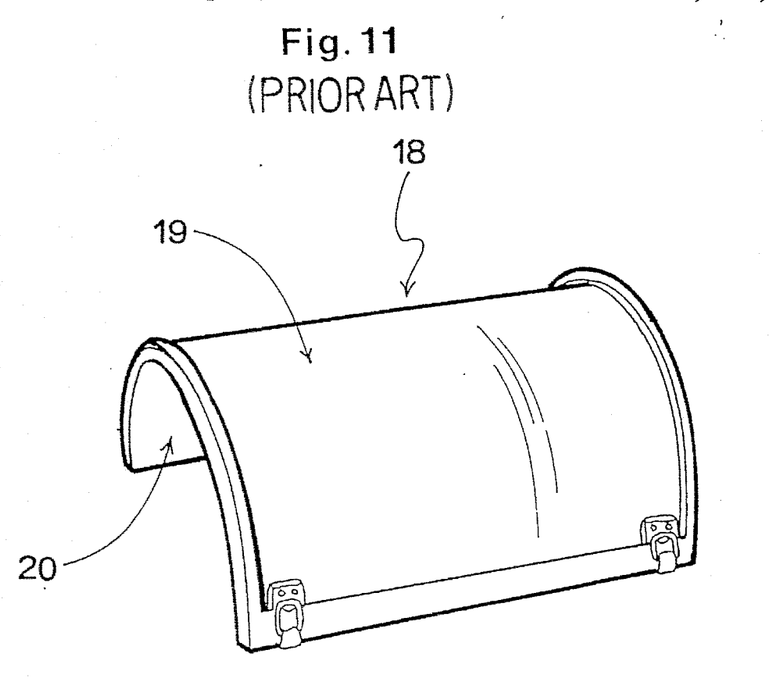
FIG. 11 is a perspective view showing an example of a prior art convexly curved cassette.
Figure 12:
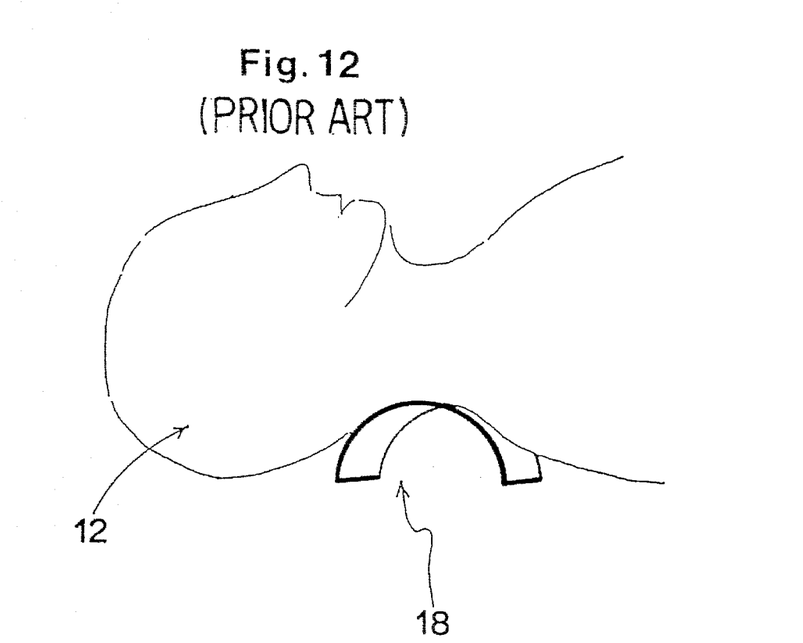
FIG. 12 is an explanatory view showing a state of the applied prior art curved cassette.

On one hand, as a film sealing case for hermetically sealing an X-ray film, such a case which is manufactured by curving a flat rectangular cassette into a convex shape as shown in FIG. 11 is available on the market. Such a convexly curved cassette 18 shown in FIG. 11 is composed of a convexly formed surface cover 19 and a back plate 20 having the same shape as that of the surface cover, and the former is hinged to the latter to form a single swing structure wherein an intensifying screen is attached to the back of the surface cover 19 and a lead plate is embedded in the back plate 20. This cassette is a special cassette for photographing a movable part of human body such as joints of neck, shoulder, knee, coxa and the like. For example, in case of a shoulder joint, the convexly curved cassette is held by a patient's armpit and then, a roentgenogram is photographed. In case of taking a roentgenogram of cervical vertebrae, the convexly curved cassette 18 is placed like a pillow under the neck of a patient 12 who lies on a horizontal stand as shown in FIG. 12, and X-ray is irradiated over the patient's throat. However, even on a flat photographic stand, the inconvenience as described above is observed and accordingly, a deformation in an X-ray pattern due to a convexly curved cassette becomes more remarkable, so that such convexly curved cassette could not have absolutely been utilized for roentgenography of vertebral columns.

Furthermore, a small-sized X-ray film being hermetically sealed with a lead foil sack is used for inserting the same into a patient's mouth in a dental field. In this case, an X-ray tube is allowed to come near the face of a patient sat on a chair, and X-ray is irradiated from the outside of patient's teeth. Under the circumstances, such film sealing case of dental use is forced onto the inside of a tooth row, so that a roentgenogram is taken in such a manner that an X-ray film has been curved in a convex shape.

Moreover, a flexible cassette which can be freely bent is available on the market for use in non-destructive inspection of a structure having a bent portion such as steel pipes and the like. In case of using such flexible cassette, the cassette is attached to a bent portion of the structure with the use of a gummed cloth tape or the like in such that the flexible cassette is curved convexly or concavely in correspondence with a curved condition of the bent portion, and a roentgenogram is taken by allowing a portable X-ray tube to come near the bent portion. However, even if such a flexible cassette is utilized by convexly or concavely curving the same, a structure involves a variety of shapes. Accordingly, such a technical idea that each of curvatures of a structure is measured one by one, and then X-ray is irradiated from the center of the circular arc thus measured has never been heretofore proposed.

OBJECTS AND SUMMARY OF THE INVENTION

The present invention has been made to solve the problems as described above, and an object of the invention is to provide a roentgenography by which a shape of a vertebral column can be clearly photographed with the use of X-ray.

Furthermore, another object of the present invention is to provide a device used for taking clearly such roentgenograms.

In order to attain the above described object, the roentgenography of vertebral columns according to the present invention comprises the steps of laying a vertebrate animal including Homo sapiens on a concavely curved X-ray film in such that the radius of curvature of said concavely curved X-ray film is equal to a distance between the X-ray film and an X-ray tube positioned over said vertebrate animal laid on the X-ray film to curve the vertebral column of said vertebrate animal into a circularly arced shape corresponding to the shape of said concavely curved X-ray film, and irradiating X-ray from said X-ray tube positioned at the center of said circular arc upon said vertebral column.

For attaining the other object as described above, the device used for executing the roentgenography of vertebral columns according to the present invention is either the one which is a curved photographic stand provided with a top having a length and a width sufficient for laying a patient thereon which is concavely curved in the longitudinal direction thereof in such that the radius of curvature of the concavely curved shape is equal to a distance between said top and an X-ray tube positioned over the curved photographic stand; or the one being a concavely curved cassette which has a length and a width sufficient for laying a patient thereon and has been curved in the longitudinal direction thereof, and the radius of curvature of said concavely curved cassette being equal to a distance between said cassette and an X-ray tube positioned over said cassette.

The present invention will be more amplified hereinbelow. That is, the invention is based on such an idea of the present inventor that if it is possible to perpendicularly project X-ray upon each of vertebrae, the above described disadvantages can be eliminated, because the more acute angle of X-ray irradiation provides the disadvantageous longer shadows of the vertebrae. In this connection, fortunately a vertebral column is flexible longitudinally and bilaterally, so that an affected part is easily curved artificially.

A film sealing case in which an X-ray film is hermetically sealed is curved into such a concave shape the radius of curvature of which is equal to a distance between the film sealing case and an X-ray tube, and a patient is laid on the film sealing case in such that the vertebral column of the patient is curved in a circularly arced shape corresponding to the aforesaid concave shape. In this situation, X-ray is irradiated from the center of the resulting circular arc upon the vertebral column of the patient.

Figure 9:
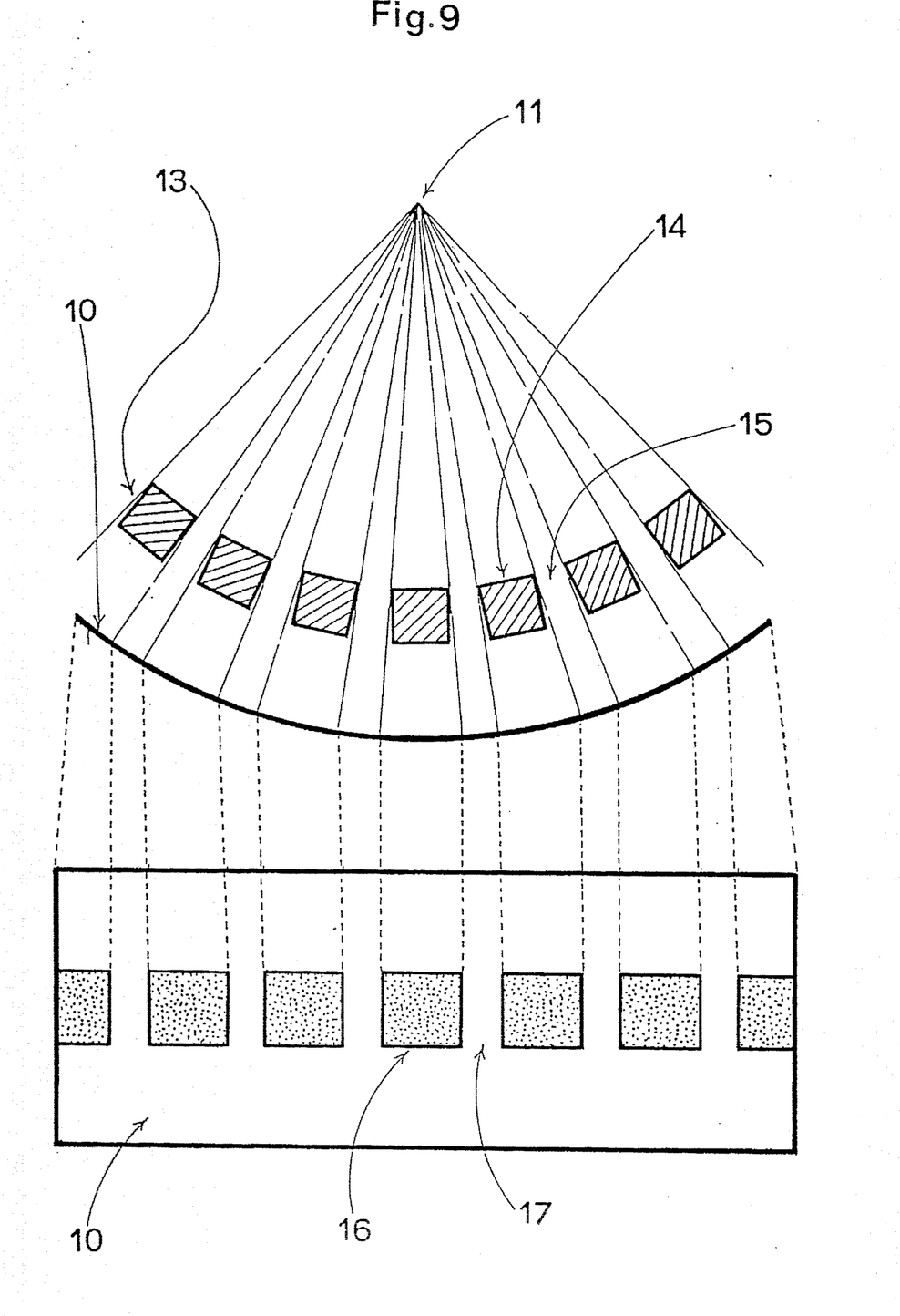
FIG. 9 is a schematic view for explaining the principle of the roentgenography according to the present invention.

When a roentgenogram is intended to take with respect to such a curved vertebral column as described above, a concavely curved X-ray film 10 and a vertebral column 13 of a patient who has been laid on the X-ray film 10 come to be positioned on a concentric circle centering around an X-ray tube 11, respectively, as shown in FIG. 9 wherein the radius of curvature of the aforesaid X-ray film 10 is equal to a distance between the film and the X-ray tube 11, and the vertebral column 13 of the patient is curved into a circularly arced shape in correspondence with the aforesaid concavely curved X-ray film 10. As a result, the X-ray to be directed to the vertebral column 13 from the center of the concentric circle is irradiated perpendicularly onto respective vertebrae 14 composing the vertebral column 13 and respective intervertebral spaces 15. Besides, shadows 16 of the respective vertebrae 14 and shadows 17 of the respective intervertebral spaces 15 are projected perpendicularly onto the X-ray film 10. Thus, the adjacent shadows 16 of the vertebrae 14 are never overlapped with each other, so that the shadows 17 of the intervertebral spaces 15 are clearly photographed on the X-ray film 10.

As a device used for executing the roentgenography of vertebral columns according to the present invention, either a curved photographic stand or a concavely curved cassette is preferred.

A first device of the curved photographic stand is the one which is prepared by curving a top of the photographic stand with a length and a width which are sufficient for laying a patient thereon in the longitudinal direction, and this top is characterized by being formed into a concave shape the radius of curvature of which is equal to a distance between the top and an X-ray tube. At the central portion of the top, a section for holding a film sealing case the profile of which is a tray-like or throughout rectangular shape may be defined thereon.

Figure 1:
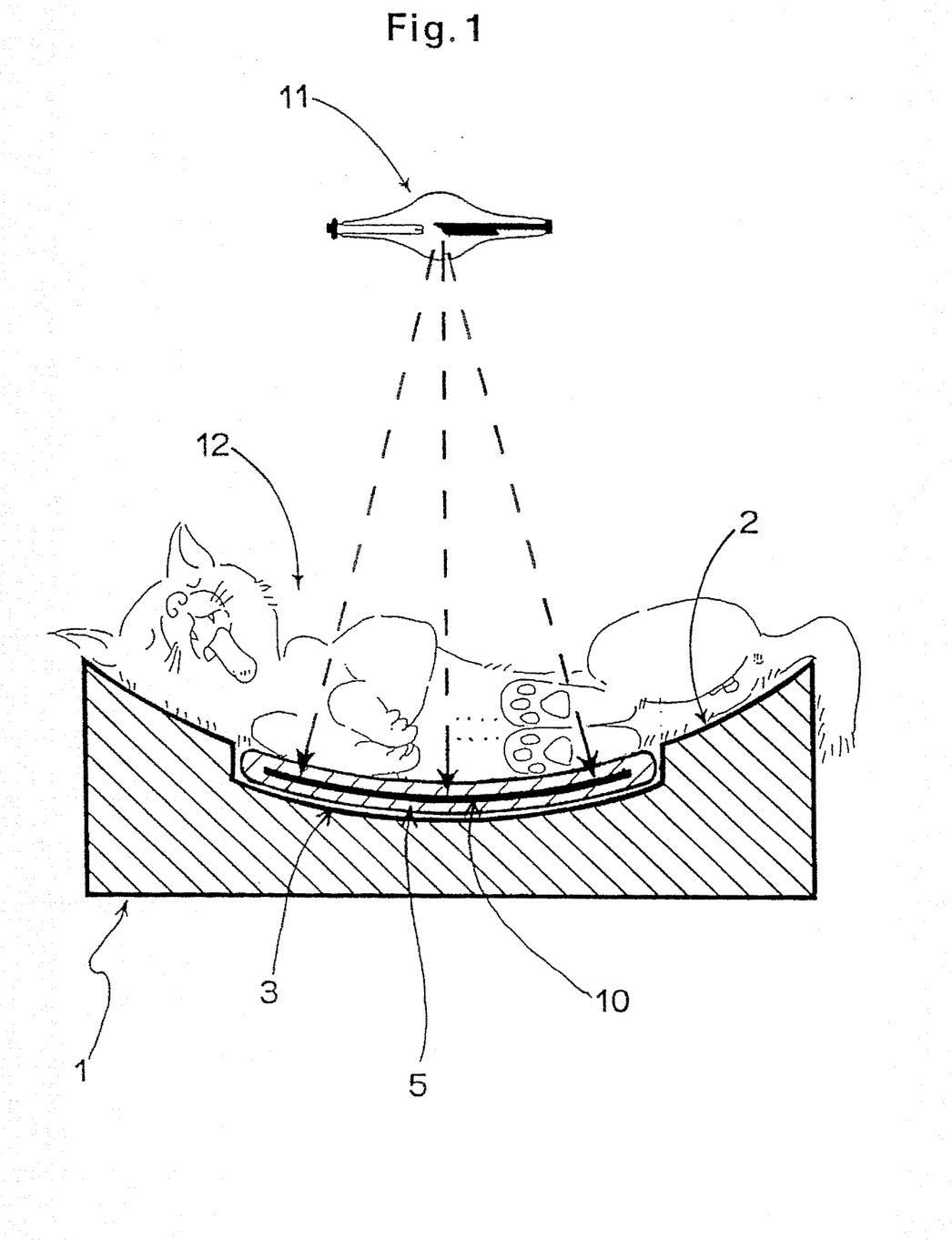
FIG. 1 is a schematic view for explaining the roentgenography according to the present invention.
Figure 2:
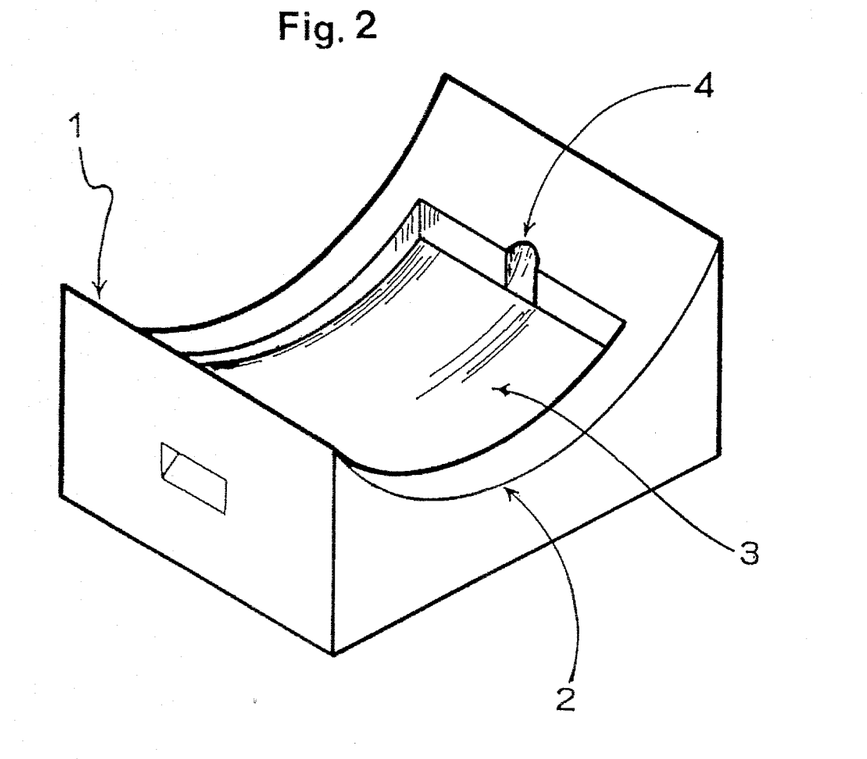
FIG. 2 is a perspective view showing the curved photographic stand according to the present invention.

According to the first device, since the curved photographic stand 1 provided with the top 2 the radius of curvature of which is equal to a distance between the top and the X-ray tube 11 is used, a film sealing case 5 in which the X-ray film has been hermetically sealed can be placed on the top 2 in close contact therewith. As a consequence, the X-ray film 10 which has been hermetically sealed in the film sealing case 5 can be curved into the concave shape, corresponding to the shape of the aforesaid curved top, the radius of curvature of which is equal to a distance between the concave shape and the X-ray tube. Furthermore, when a patient 12 is laid simply on his (her) side or back on the curved film sealing case 5, the vertebral column of the patient 12 can be curved into a moderate circularly arced shape so as to correspond to the radius of curvature of the X-ray film 10.

on one hand, when a compact film sealing case 5 in which an X-ray film has been hermetically sealed is contained in a tray-like or throughout rectangular-shaped section 3 for holding the film sealing case which is defined on the top 2 of the photographic stand 1, it can be arranged in such that the thick film sealing case 5 does not protrude the surface of the top 2. Accordingly, corners of the film sealing case 5 do not form a difference in level on the top 2. As a result, even if a part of a vertebral column such as cervical vertebrae, lumbar vertebrae or the like is photographed, the vertebral column of the patient 12 can be curved into a circularly arced shape.

A concavely curved cassette being a second device is prepared by curving a cassette composed of a base plate and a back cover each having a length and a width being capable of sealing an X-ray film in the longitudinal direction. The concavely curved cassette is characterized by that both the base plate and the back cover are formed into a concave shape the radius of curvature of which is equal to a distance between the cassette and an X-ray tube. Either the back cover or a pair of divided back covers may be hinged on the base plate so as to form a single swing cover or a pair of swing covers each being openable in a direction from the central portion to the opposite end of the base plate.

Figure 3:
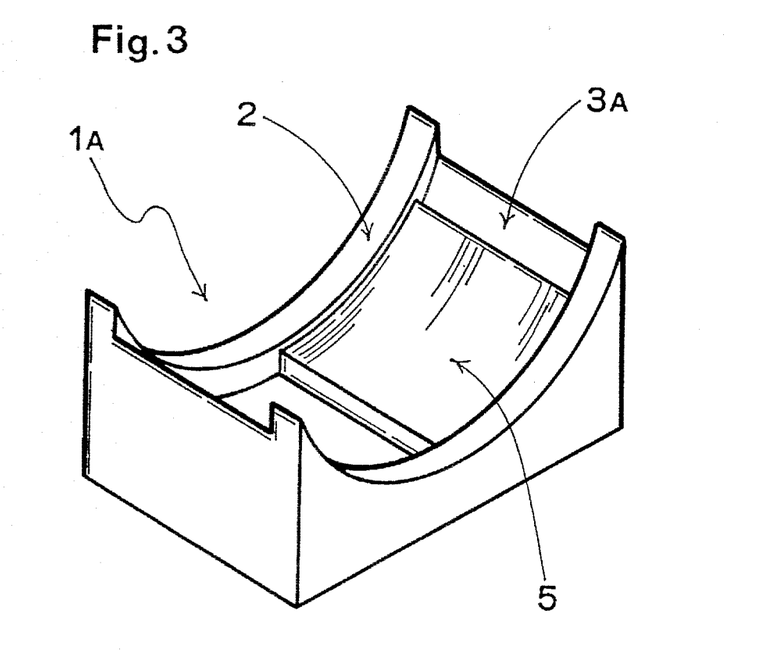
FIG. 3 is a perspective view showing a modification of the curved photographic stand according to the present invention.
Figure 5:
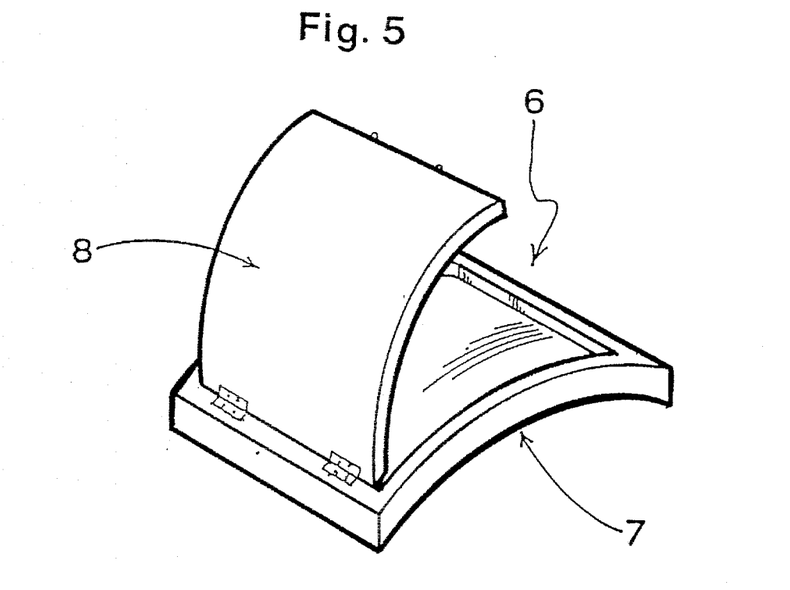
FIG. 5 is a perspective view showing the concavely curved cassette according to the present invention.
Figure 6:
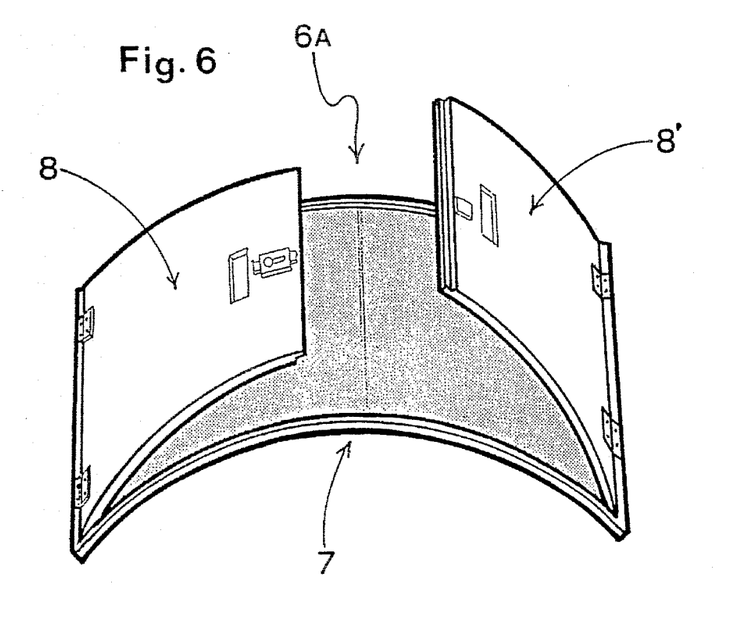
FIG. 6 is a perspective view showing a modification of the concavely curved cassette according to the present invention.
Figure 7:
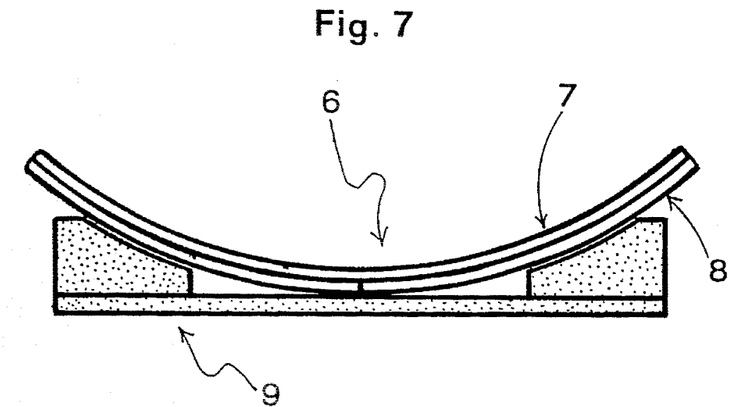
FIG. 7 is a side view showing a state of the applied concavely curved cassette according to the present invention.

According to the second device shown in FIG. 5 or 6, the concavely curved cassette 6 the radius of curvature of which is equal to a distance between the cassette and an X-ray tube has the same functions as that of the curved photographic stand 1 shown in FIG. 2 or 3, whereby an X-ray film can be curved into a circularly arced shape together with the vertebral column of a patient. When the concavely curved cassette 6 is rested on a horizontal stand in such that the concave surface of the cassette faces upwards, the cassette might swing unstably in seesaw-like movement. However, such curved cassette can be stably held by either a cassette holding stand 9 as shown in FIG. 7, or a pair of fixing blocks (not shown) each having a suitable profile which support the cassette from the convex side thereof, respectively.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The roentgenography of vertebral columns of vertebrate animal according to the present invention will be described in detail by describing the preferred embodiments of the devices used for executing the roentgenography of the present invention hereinbelow.

The roentgenography according to the present invention is carried out by the use of either the first device of a curved photographic stand, or the second device of a concavely curved cassette.

The best mode for the device is the first device of the curved photographic stand 1 shown in FIGS. 1 and 2. The curved photographic stand 1 is made from a synthetic resin, a light metal or the like, and the stand 1 is disposed on a flat floor or a conventional flat photographic stand for applying the same in roentgenography. The top 2 of the curved photographic stand 1 is defined in a concave shape in such that the radius of curvature thereof is equal to a distance between the top 2 and an X-ray tube 11. The concave shape is preferable to be a circular arc having a radius of curvature of about 1 meter in the case where a patient is a small animal such as dog, cat or the like. While a length and a width of the top 2 may be selected suitably dependent upon types and sizes of patients, it is desirable that the top 2 has generally a size which is sufficient for laying the whole body of a patient thereon.

On the central portion of the top 2, a tray-like section 3 for holding a film sealing case is defined. In order that a compact film sealing case 5 contained in the tray-like section 3 does not protrude or retract from the surface of the top 2, the bottom of the film sealing case holding section 3 is also formed in the same concave shape as that of the top 2, and the depth of the top 2 is made equal to the thickness of the film sealing case holding section 3. Furthermore, notched portions 4 each having a suitable profile for inserting a finger thereinto may be defined on the opposite ends of the film sealing case holding section 3 as shown in FIG. 2 in order to attach and detach easily the film sealing case 5 thereto and therefrom.

The compact film sealing case 5 for partially photographing an affected part is contained in the film sealing case holding section 3 thus defined, and a patient 12 is laid on the top 2. Then, a position of the patient 12 is adjusted in such that the affected part thereof is appropriately positioned on the film sealing case 5, and thereafter X-ray is irradiated thereon. Consequently, a part of a vertebral column such as only cervical vertebrae, lumbar vertebrae or the like can be partially photographed, so that a large-sized X-ray film becomes unnecessary and it results in saving on X-ray film expenses.

As the film sealing case 5, a flexible cassette and a lead foil bag which are freely bendable, respectively, or the concavely curved cassette 6 shown in FIG. 5 which has been formed in a concave shape having the same curvature as that of the concave of the top 2 and the like device may suitably selected for the application. In addition, both types of the film sealing cases of the present invention may be properly used, i.e. the compact film sealing case 5 for photographing partially a vertebral column such as cervical vertebrae, lumbar vertebrae and the like or a larger-sized film sealing case 5A shown in FIG. 4 being used for taking a panoramic roentgenogram of the whole body of a patient may be selected.

When the bendable film sealing case 5 such as a flexible cassette, a lead foil bag or the like is contained in said film sealing case holding section 3 and a patient is laid thereon, the film sealing case 5 comes to be in closely contact with the bottom of the film sealing case holding section 3 due to the body-weight of the patient. As a result, the X-ray film 10 contained in the film sealing case 5 is concavely curved in such that the radius of curvature of the concaved X-ray film 10 is equal to a distance between the film and the X-ray tube 11. Simultaneously, the vertebral column of the patient 12 is also concavely curved with the same curvature as that of the X-ray film 10. Thus, the X-ray film 10 and the vertebral column of the patient come to be position on a concentric circle centering around the X-ray tube 11, so that the roentgenography according to the present invention can positively be executed. In the case of using the concavely curved cassette 6 formed so as to be in closely contact with the top 2, the same effect as that of the bendable film sealing case can also be obtained.

Next, a modification of the first device will be described hereinbelow.

In a curved photographic stand 1A shown in FIG. 3, a throughout rectangular section 3A for holding a film sealing case is defined on the top 2 of the curved photographic stand. According to the throughout rectangular section thus defined, a compact film sealing case 5 may be slidably moved along the whole length of the rectangular section extending over from the right to left ends of the top 2 as shown in FIG. 3. If there is a gap as shown in FIG. 3, a packing such as a rubber plate and the like having the same thickness as that of the film sealing case 5 is disposed therein. When such a curved photographic stand is used, the vertebral column of the patient 12 can be partially photographed by suitably selecting a position to be photographed, even if a position of the patient 12 is not adjusted.

Figure 4:
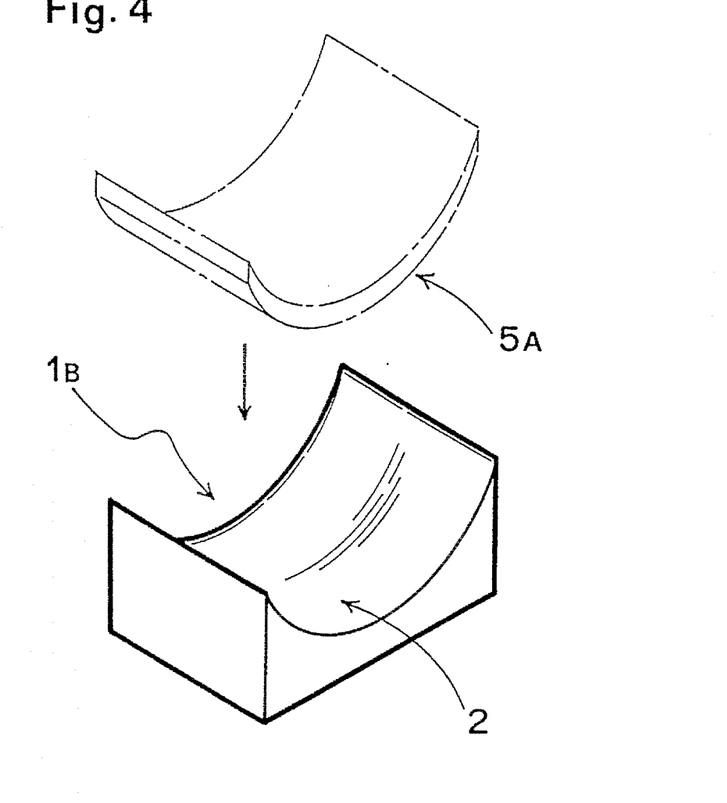
FIG. 4 is a perspective view showing another modification of the curved photographic stand according to the present invention.

Moreover, no film sealing case holding section is defined on a top 2 of a curved photographic stand 1B being another modification of the present invention shown in FIG. 4.

Furthermore, it was surprisingly found that not only the whole of a vertebral column, but also a panoramic roentgenogram of the whole body skeleton of a patient could be taken in the case when a large-sized film sealing case 5A having a length and a width within which the whole body of the patient can be laid is disposed on each of the tops 2 of the curved photographic stand 1B shown in FIG. 4, the stand 1 shown in FIG. 2, and the stand 1A shown in FIG. 3, respectively.

More specifically, when it is intended to obtain an X-ray pattern of the whole body of a patient by the use of a conventional flat photographic stand, it is required to separately take roentgenograms with respect to the head, the breast, the abdomen and the like of a patient, and to link the respective roentgenograms taken one another in order to eliminate such disadvantage in that the skeletons photographed become obscure at the edge portions of the films, whereby very complicated works have been necessary heretofore.

In this respect, there is a mere use for surveying a skeleton of the whole body from the scientific point of view, so that no technical idea for putting such panoramic roentgenogram to practical use in emergent diagnosis has never been proposed heretofore. More specifically, in the event of an emergency case of a traffic accident, when a veterinary surgeon touches carelessly an animal patient who cannot talk to determine which part of which bone is broken, there is a case where the veterinary surgeon is bitten by the animal patient and this is very dangerous. For this reason, it has been inevitably required to take from several to several tens of roentgenograms throughout the whole body of a patient in an animal clinic in order to investigate existence of a fracture or a damaged area. According to the roentgenography of the present invention, it was found unexpectedly that an X-ray pattern of the whole body of a patient could be taken easily with only one outsized film. In accordance with the panoramic roentgenography of the present invention, when only one each roentgenogram is taken in a state where a patient is laid on his (her) back and side, respectively, the whole body skeleton of the patient can be observed obviously from two directions. As a consequence, it becomes possible to take a prompt treatment in an emergency case so that a remarkable advantage to elevate markedly a ratio of life-saving can be attained.

Next, embodiments of the second device according to the present invention shown in FIGS. 5 through 8 will be described hereinbelow.

The second device differs from the above described first device in that no curved photographic stand 1 is used, but only the concavely curved cassette 6 is used to maintain an X-ray film together with a vertebral column of a patient in a prescribed radius of curvature. In other words, the cassette itself is curved in a concave shape the radius of curvature of which is equal to a distance between said cassette and an X-ray tube, so that the X-ray film can be held in the concave shape having a prescribed radius of curvature without using a curved photographic stand. Furthermore, when a patient is laid on the concaved surface of the concavely curved cassette 6, the vertebral column of the patient can also be curved in the circularly arced state. Thus, according to the second device, the roentgenography of the present invention in which an X-ray pattern is obtained by photographing the concavely curved vertebral column of a patient on the concavely curved X-ray film positioned on such a concentric circle centering around an X-ray tube can be positively carried out as in the case of the first device.

A concavely curved cassette 6 is produced by pouring carbon fiber or a synthetic resin into a frame molded in a prescribed radius of curvature. In this case, it must be sufficiently check a strength and a thickness of a material to be used for such cassettes, because if a cassette thereof is bent due to the body-weight of a patient in case of the application thereof, the radius of curvature of the cassette changes, whereby the above described object comes to be not attained.

The concavely curved cassette 6 shown in FIG. 5 is the one being a single swing cover type composed of a base plate 7 and a back cover 8 formed into a concave shape the radius of curvature of which is equal to a distance between the cassette and an X-ray tube, and an end of the back cover 8 is hinged to the base plate 7. In a conventional convexly curved cassette 18 as shown in FIG. 11, an intensifying screen is attached to the back of a surface cover 19, and a lead plate is embedded in a back plate 20. On the contrary, in case of the concavely curved cassette 6, an intensifying screen is attached to the back of the surface cover 7, and a lead plate is embedded in the back cover 8. In another modification, it may be arranged in such that an intensifying screen and a lead plate are separated from a cassette to be detachable thereto, and in case of application of the cassette, the intensifying screen, an X-ray film and the lead plate are superposed on the back of the surface plate 7 in order, then they are covered with the back cover 8 to hermetically seal these components.

The concavely curved cassette 6A shown in FIG. 6 is the one of a type of a pair of swing covers wherein a pair of right and left back covers 8 and 8' are opened swingably at the central part of the cassette. In this arrangement, the back covers opened oppositely do not occupy much more space than that in case of using a single swing cover type cassette. For this reason, when an oversized film for panoramic photograph is hermetically sealed into a cassette, an operation therefor can easily be conducted in even a narrow darkroom. Furthermore, in such a case where a customized outsize film is out of stock, and a substitution of two X-ray films on the market by joining together them for the customized outsize film is unavoidably intended, the joint can be precisely arranged. More specifically, since X-ray films have considerably high elasticity, it has been very difficult to align the joints of two films in a concavely curved cassette of a single swing cover type. On the other hand, when the concavely curved cassette 6A of a type of a pair of oppositely swing covers is used, it is possible that a first film is placed on the base plate 7 and one 8 of the back covers is closed, thereafter the other back cover 8' is closed while aligning an end of a second film to that of the first film. Accordingly, the jointed ends of two films can positively be aligned to be hermetically sealed in the cassette. Because of this arrangement, the resulting jointed ends of the films do not interfere with the X-ray pattern photographed.

Figure 8:
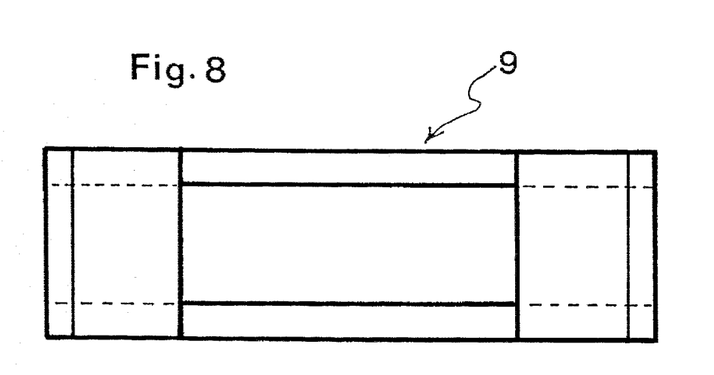
FIG. 8 is a plan view showing the cassette holding stand according to the present invention.

When a vertebral column or the whole body of a patient is photographed by the use of the above described concavely curved cassette 6, the cassette holding stand 9 shown in FIGS. 7 and 8 is disposed on a horizontal stand, and the concavely curved cassette 6 is rested thereon in such that the back cover 8 directs the underside thereof. Thus, the concavely curved cassette 6 which is usually swung unstably in seesaw-like movement can be stably positioned under an X-ray tube. While an example of the cassette holding stand 9 is specifically shown in FIGS. 7 and 8, the profile of which is not limited thereto. Furthermore, although there is no illustration, the concavely curved cassette 6 may be supported by a pair of fixing blocks each having a suitable profile and positioned on the opposite ends of the cassette.

According to the present invention, roentgenograms of a vertebral column shape of a patient can be clearly taken. Accordingly, an affected part of, for example, disc hernia and the like can positively be diagnosed by only one photographing, so that operations for photographing and reading the photograph become simple and easy, resulting in reduction of expenses for films and development thereof, besides it brings about such an advantage that an amount of X-ray with which a patient is inevitably to be irradiated can be suppressed as much as possible. As a matter of course, the roentgenography and the devices used therefor according to the present invention exhibit also influences upon diagnosis for spinal damages such as fracture, dislocation and the like, spondylolisthesis, spinal caries, spinal tumor and the like. Furthermore, the present invention is applicable for all the other flexible skeletons such as ribs, ossa digitus manus and pedis, caudal vertebrae and the like, so that this invention can also be contributed to the progress in osteometry.

In addition, the present invention provides unexpectedly such advantage in that a panoramic photograph of skeletons of the whole body of a patient can be taken with only one outsize film. Thus, it becomes possible to diagnose existence of a fracture or a degree of the damage thereof in an emergency case due to a traffic accident and the like, and particularly to diagnose an animal patient who cannot talk, whereby an exact first-aid treatment can be given to the patient.

It will be appreciated by those of ordinary skill in the art that the present invention can be embodied in other specific forms without departing from the spirit or essential characteristics thereof.

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A roentgenography of the vertebral column of a patient comprising the steps of laying said patient on a concavely curved X-ray film set on the top of a semi-ring curved photographic stand in such that radius of curvature of said concavely curved X-ray film is equal to a distance between said X-ray film and X-ray tube positioned over said patient laid on the X-ray film to curve the vertebral column of said patient into a circularly arched shape corresponding to the shape of said concavely curved X-ray film, and irradiating X-ray from said X-ray tube positioned at the center of said circular arch upon said vertebral column.

2. A device used for executing the roentgenography as claimed in claim 1 comprising a semi-ring curved photographic stand being provided with a top of having a length and a width sufficient for laying a patient thereon which is concavely curved in the longitudinal direction thereof in such that the radius of curvature of the concavely curved shape is equal to a distance between said top and an X-ray tube positioned over the semi-ring curved photograph stand.

* * * * *